(12) United States Patent
Lancelle

(10) Patent No.: US 12,178,672 B2
(45) Date of Patent: Dec. 31, 2024

(54) METHOD FOR EXPORTING A THREE-DIMENSIONAL ESTHETIC DENTAL DESIGN MODEL FROM AN AUGMENTED REALITY APPLICATION TO A COMPUTER-AIDED DESIGN APPLICATION

(71) Applicant: Ivoclar Vivadent AG, Schaan (LI)

(72) Inventor: Marcel Lancelle, Zürich (CH)

(73) Assignee: Ivoclar Vivadent AG, Schaan (LI)

( * ) Notice: Subject to any disclaimer, the term of this patent is extended or adjusted under 35 U.S.C. 154(b) by 323 days.

(21) Appl. No.: 17/720,683

(22) Filed: Apr. 14, 2022

(65) Prior Publication Data

US 2022/0338966 A1 Oct. 27, 2022

(30) Foreign Application Priority Data

Apr. 23, 2021 (EP) ..................................... 21170126

(51) Int. Cl.
| | | |
|---|---|---|
| A61C 13/00 | (2006.01) | |
| A61B 5/00 | (2006.01) | |
| A61B 90/00 | (2016.01) | |
| A61C 7/00 | (2006.01) | |
| A61C 9/00 | (2006.01) | |

(Continued)

(52) U.S. Cl.
CPC ........ A61C 13/0004 (2013.01); A61B 5/0088 (2013.01); A61B 5/4547 (2013.01); A61B 90/36 (2016.02); A61C 7/002 (2013.01); A61C 9/0053 (2013.01); G06F 30/10 (2020.01); G06T 19/20 (2013.01); A61B 2090/365 (2016.02); G06F 2111/18 (2020.01); G06F 2111/20 (2020.01);

(Continued)

(58) Field of Classification Search
CPC . A61B 2090/365; A61B 5/4547; A61C 7/002; G06F 30/10; G06F 2111/20; G06T 19/20; G06T 2219/2004; G06T 2219/2016
USPC .......................................................... 700/98
See application file for complete search history.

(56) References Cited

U.S. PATENT DOCUMENTS 9,775,491 B2 * 10/2017 Clausen .................... A61B 1/24
10,835,361 B2 * 11/2020 Fisker ................... A61B 5/1111
(Continued)

FOREIGN PATENT DOCUMENTS

| EP | 3629336 A1 | 4/2020 | |
|---|---|---|---|
| WO | WO-2019133583 A1 * | 7/2019 | ............. A61B 34/00 |
| WO | WO-2019162164 A1 * | 8/2019 | ............. A61B 90/36 |

OTHER PUBLICATIONS

Augmented Reality Navigation With Automatic Marker-Free Image Registration Using 3-D Image Overlay for Dental Surgery; 10 pages; Wang et al.; IEEE Transactions On Biomedical Engineering, vol. 61, No. 4, Apr. 2014.*

(Continued)

*Primary Examiner* — Ronald D Hartman, Jr.
(74) *Attorney, Agent, or Firm* — Ann M. Knab; Thad McMurray

(57) ABSTRACT

A method for exporting a three-dimensional dental design model based on a three-dimensional dental library model (4) from an augmented reality application (6) which is adapted to visualize an image of the dental library model (4) rendered by a virtual camera with a preliminary pose and scale in a photo (2) of a face of a patient taken by a camera under a viewing axis to the face of the patient, the photo (2) including a mouth opening showing at least part of the present situation of the patient's dentition.

13 Claims, 4 Drawing Sheets

(51) Int. Cl.
*G06F 30/10* (2020.01)
*G06F 111/18* (2020.01)
*G06F 111/20* (2020.01)
*G06T 19/20* (2011.01)

(52) U.S. Cl.
CPC ............... *G06T 2219/2004* (2013.01); *G06T 2219/2016* (2013.01)

(56) References Cited

U.S. PATENT DOCUMENTS

| | | |
|---|---|---|
| 10,980,621 B2* | 4/2021 | Lancelle ............... A61C 9/0046 |
| 11,083,552 B2 | 8/2021 | Lancelle et al. |
| 11,213,374 B2 | 1/2022 | Lancelle et al. |
| 11,244,519 B2 | 2/2022 | Lancelle et al. |
| 2013/0218530 A1 | 8/2013 | Deichmann |
| 2019/0254789 A1* | 8/2019 | Lancelle ............... A61C 9/0046 |
| 2022/0370170 A1* | 11/2022 | Shanjani ............... A61C 13/34 |

OTHER PUBLICATIONS 3D dental image registration using exhaustive deformable models: a comparative study; Kalla et al.; 14 pages; Dentomaxillofacial Radiology (2017) 46, 20160390; 2017 The Authors. Published by the British Institute of Radiology.*

* cited by examiner

METHOD FOR EXPORTING A THREE-DIMENSIONAL ESTHETIC DENTAL DESIGN MODEL FROM AN AUGMENTED REALITY APPLICATION TO A COMPUTER-AIDED DESIGN APPLICATION

CROSS-REFERENCE TO RELATED APPLICATIONS

This application claims priority to European Patent Application No. 21170126.3 filed on Apr. 23, 2021, the disclosure of which is incorporated herein by reference in its entirety.

Technical Field

The present invention pertains to a method for exporting a three-dimensional dental design model based on a three-dimensional dental library model from an augmented reality application, the augmented reality application being adapted to visualize on a display a rendered image of the dental library model which has been rendered by a virtual camera with a preliminary pose and scale in a photo of a face of a patient taken by a camera under a viewing axis to the face of the patient, the photo including a mouth opening showing at least part of the present situation of the patient's dentition, the method including:

placing within the augmented reality application the dental library model on the photo and providing tools to modify and/or move the dental library model on the display to obtain a desired dental design model, providing a three-dimensional scan model of the present situation of the patient's dentition, aligning the scan model and the present situation of the patient's dentition in the photo to obtain a pose of the scan model, calculating, based on the preliminary pose and scale and the pose of the scan model, at least one transformation to bring the desired dental design model and the scan model into a common coordinate system.

Background

For dentists and patients, it is of interest to get a visual impression of the appearance of the face with a modified situation of dentition, i.e. to visualize the modified situation of dentition in a photo of the face of the patient. Also, the appearance during or after a dental or orthodontic treatment may be of importance for the patient before deciding to undergo such treatment. For this purpose, a virtual preview (virtual mockup) of the dentition modified by a dental or orthodontic treatment and/or a preview of the patient wearing the braces/retainers is helpful for the dentist and may also be used in the course of interactively modifying the treatment plan to get the most favorable esthetic results. In addition to the visualization of the situation of dentition in a single photo, it can be helpful to visualize the situation of dentition in several photos e.g. from several angles or with different expressions. Also, a video of real-time life stream such as an Augmented Reality setup can be used.

U.S. Pat. Nos. 10,980,621, 11,213,374, 11,083,552, 11,244,519 and 20130218530 are directed to computer based methods used in the production of dental applications and products and are hereby incorporated by reference in their entirety.

In the context of the present invention, the term "denture" is not necessarily restricted to full dentures but also comprises partial dentures, orthodontic situations or adaptations, or dental restorations such as dental prostheses, including crowns, crown lays, veneers, inlays and onlays, bridges, dental implants, and implant restorations. Accordingly, the term "dental model" includes all models of dental prostheses—such as models of complete and partial dentures—that are used for prosthodontic purposes but also all models of dentitions modified by orthodontic treatments.

In this respect EP 3 629 336 A1 discloses a method for exporting a three-dimensional dental design model based on a three-dimensional dental model, which could be especially a dental library model, from an augmented reality application. The augmented reality application is adapted to visualize on a display an image of the dental library model rendered by a virtual camera with a preliminary pose and scale in a photo of a face of a patient taken by a camera under a viewing axis to the face of the patient. The photo includes a mouth opening showing the present situation of the patient's dentition. The described method comprises as a first step placing within the augmented reality application the rendered image of the dental library model on the photo and providing tools to modify the dental library model on the display. With these tools, a doctor can in presence of the patient, remotely or without the patient, modify and/or move the design of the dental library model on the display to obtain a desired dental design model. The method comprises as next steps providing a three-dimensional scan model of the present situation of the patient's dentition, aligning a rendered image of the scan model and the present situation of the patient's dentition in the photo to obtain a pose of the scan model, and calculating, based on the preliminary pose and scale and the pose of the scan model, at least one transformation to bring the desired dental design model and the scan model into a common coordinate system. It has been found that the three-dimensional dental design model, obtained by the described method and exported to a computer-aided design application, matches reasonably the situation of the present dentition of the patient in the visible region, e.g. the area of the incisors but usually badly matches the situation of the present dentition of the patient in the less visible molar region. This is due to the fact that the user of the augmented reality application designs the desired dental design model on the display which enables the user to align the teeth at the well visible region much better than the teeth at the less visible or invisible molar region.

Summary

It is an object of the present invention to provide a method for exporting a three-dimensional dental design model that matches the situation of the present dentition of the patient in the visible region as well as in the less visible molar region wherein the dental design model is an esthetic dental design model that is to be exported from an augmented reality application to another application, e.g. a computer-aided design application.

This object is achieved by the method comprising the features of the claims. Preferred embodiments of the invention are set out in the dependent claims.

In accordance with the present invention, non-rigid deformations are applied to adapt the positioned dental design model to the scan model by minimizing a measure of shape difference between the positioned dental design model and the scan model to obtain a modified dental design model as the dental design model for export.

In computer graphics, a three-dimensional model is the product of the process of developing a mathematical representation of any object in three-dimensions. There are several ways to represent an object. The method used herein is polygonal modelling of the outer surface but other methods as e.g. curve modelling are also thinkable. Polygonal modelling is a method for modelling objects by representing their surfaces using polygon meshes. Polygon meshes comprise vertices, edges and faces that define the shape of the object. Vertices are points in three-dimensional space. The vertices are connected by line segments that are called edges. The polygons formed by the vertices and the edges can be called faces and are usually triangular but also other polygons as e.g. quadrilaterals are thinkable.

According to one embodiment, visible and non-visible regions of the positioned dental design model are determined by taking into account the position in respect to the mouth opening and the viewing axis. The viewing axis can be assumed as perpendicular to the image plane of the photo. In general, the viewing axis is the axis from the camera, with which the photo was taken, to the face or dentition of the patient. Weighted non-rigid deformations are used to adapt the positioned dental design model to the scan model. Movements caused by the non-rigid deformations can be divided into movements along the viewing axis and movements perpendicular to the viewing axis wherein the viewing axis is the viewing axis of the camera that took the photo of the face, and by using weighted non-rigid deformations, movements, that are perpendicular to the viewing axis and caused by the non-rigid deformation, are restricted more for the vertices of visible regions than such movements for the vertices of the non-visible regions. This is achieved by applying low weights to movements perpendicular to the viewing axis of the vertices of the visible regions and higher weights to movements perpendicular to the viewing axis of the vertices of the non-visible regions to obtain a modified dental design model. This non-rigidly deformed model with minimized measure of shape difference to the scan model is the dental design model that can be exported to e.g. a computer-aided design application.

According to another embodiment of the method the visible regions are in particular front regions including incisors and the non-visible regions are in particular rear regions including molars. Weighted non-rigid deformations are used to adapt the positioned dental design model to the scan model. By using weighted non-rigid deformations, movements, that are perpendicular to the viewing axis and caused by the non-rigid deformation, are restricted more for the vertices of the front regions including incisors than such movements for the vertices of the rear regions including molars. This is achieved by applying low weights to movements perpendicular to the viewing axis of the vertices of the front regions and higher weights to movements perpendicular to the viewing axis of the rear regions to obtain a modified dental design model. This non-rigidly deformed model with minimized measure of shape difference to the scan model is the dental design model that can be exported to e.g. a computer-aided design application.

According to one embodiment of the method, the weights that are used in the weighted non-rigid deformations and are applied to movements perpendicular to the viewing axis of the vertices of the positioned dental design model, gradually increase from the visible regions to the non-visible regions.

According to one embodiment of the method, the weights that are used in the weighted non-rigid deformations and are applied to movements perpendicular to the viewing axis of the vertices of the positioned dental design model, gradually increase from the front regions including the vertices of the incisors to the rear regions including the vertices of the molars. This ensures that the incisors are moved less than the molars.

According to another embodiment of the method, movements along the viewing axis caused by the weighted non-rigid deformations are treated differently than movements perpendicular of the viewing axis. Movements along the viewing axis are allowed for all vertices of the positioned dental design model. This is achieved by allowing to apply the same high weights to movements along the viewing axis of all vertices of the positioned dental design model.

By allowing movements along the viewing axis the distance between the positioned dental design model and a virtual camera can be adapted. It is assumed that the scan model and the positioned dental design model should be at a similar distance to the virtual camera. Allowing movements along the viewing axis solves a potential problem that might occur when an inexperienced user designs the desired dental design model in an augmented reality application on a display and relates to an apparent size of the model in the augmented reality application. Although the desired dental design model may look correct, it could be too far in the front (and thus be smaller than intended) or too far behind the scan model (and thus be larger than intended). To be able to correct this distance by applying weighted non-rigid deformations, the weights are configured to allow movements along the viewing axis.

According to another embodiment of the method, non-rigid deformations comprise shearing, skewing, uniform and/or non-uniform scaling.

Applying weighted non-uniform deformations allows having significant control over movements of the positioned dental design model. The positioned dental design model can be deformed to the scan model while at the same time the desired dental design model the user designed in the augmented reality application can be preserved to a large extent. There are several options to per form weighted non-rigid deformations in order to achieve non-rigid alignment. The deformations can be performed by methods that are also known as non-rigid registration or non-rigid alignment, e.g. by computing a surface registration (e.g. as-rigid-as-possible or iterative closest points) or by deforming the space (e.g. by cage deformation or by deformation with radial basis functions). It is also possible to apply multiple deformations one after another to achieve the desired deformation.

In each deformation method weights can be applied to restrict and/or allow movements in different directions for each vertex of the positioned dental design model individually.

In certain cases, it is desirable to fully preserve the shape of certain areas of the positioned dental design model, e.g. of individual teeth. This is particularly important when intending to use prefabricated teeth with a given geometry that cannot be changed. The adaption of the teeth is then only done by individual translation and rotation of each tooth. It is of great importance to be able to adapt the weights suitable for each patient case and in particular for each vertex of each tooth individually. In addition, it may be useful in certain cases to perform a collision detection to avoid self-intersections.

In a preferred embodiment, the method comprises exporting the modified dental design model to another application. In particular, exporting comprises generating an export file comprising the modified dental design model. The modified dental design model is exported in a file with a defined coordinate system, or together with the scan model. The other application is an external application and is e.g. a computer-aided design application. Furthermore, STL is the common file format for the export file.

The invention also pertains to a computer programme product comprising programme code which is stored on a machine-readable medium a non-transitory machine-readable medium, or being embodied by an electromagnetic wave comprising a programme code segment, and having computer-executable instructions for performing the method described above.

In another method, a three-dimensional scan model of the present situation of the patient's dentition is retrieved before using the augmented reality application. The next step of the method comprises adapting the three-dimensional dental library model to the scan model with non-rigid deformations by minimizing a measure of shape difference between the three-dimensional dental library model and the scan model to obtain a modified dental library model. The deformations are less restricted as in the method described above as there is no already performed design step to be taken into account. However, it may be desirable to keep a symmetry and/or regularity instead of perfectly matching the library model to the scan model. The result of this step is a modified dental library model which can already have the correct size. The method comprises as a next step placing within the augmented reality application a rendered image of the modified dental library model on the photo and providing tools to modify and/or move the modified dental library model on the display. With these tools, a doctor can in presence of the patient, remotely or without the patient, modify the design of the modified dental library model to obtain a desired dental design model. Because the modified dental library model is already adapted to the scan model of the patient by non-rigid deformations, the visualization of this model on the photo in the augmented reality application is more realistic. Consequently, designing a desired dental design model based on the modified dental library model requires less time compared to designing a desired dental design model based on a dental library model. The reason for this is that fewer adjustments are needed because the modified dental library model is already adapted to the scan model and therefore already matches reasonably the dentition of the patient and thus the situation of the patent's dentition in the photo. The method comprises as next steps aligning the scan model and the present situation of the patient's dentition in the photo to obtain a pose of the scan model, and calculating, based on the preliminary pose and scale and the pose of the scan model, at least one transformation to bring the desired dental design model and the scan model into a common coordinate system, in particular wherein the desired dental design model is brought to a coordinate system of the scan model to obtain a positioned dental design model.

According to one embodiment of the method, weighted non-rigid deformations are used to adapt the three-dimensional dental library model to the scan model.

According to another embodiment of the method, non-rigid deformations comprise shearing, skewing, uniform and/or non-uniform scaling.

In a preferred embodiment, the method comprises exporting the modified dental design model to another application. In particular, exporting comprises generating an export file comprising the modified dental design model. The modified dental design model is exported in a file together with the scan model. The other application is an external application and is e.g. a computer-aided design application. Furthermore, STL is the preferred file format for the export file.

The invention also pertains to a computer programme product comprising programme code which is stored on a machine-readable medium, or being embodied by an electromagnetic wave comprising a programme code segment, and having computer-executable instructions for performing methods described above.

BRIEF DESCRIPTION OF THE DRAWINGS

The invention in the following will be described in detail by referring to exemplary embodiments that are accompanied by figures, in which.

DETAILED DESCRIPTION

Figure 1:
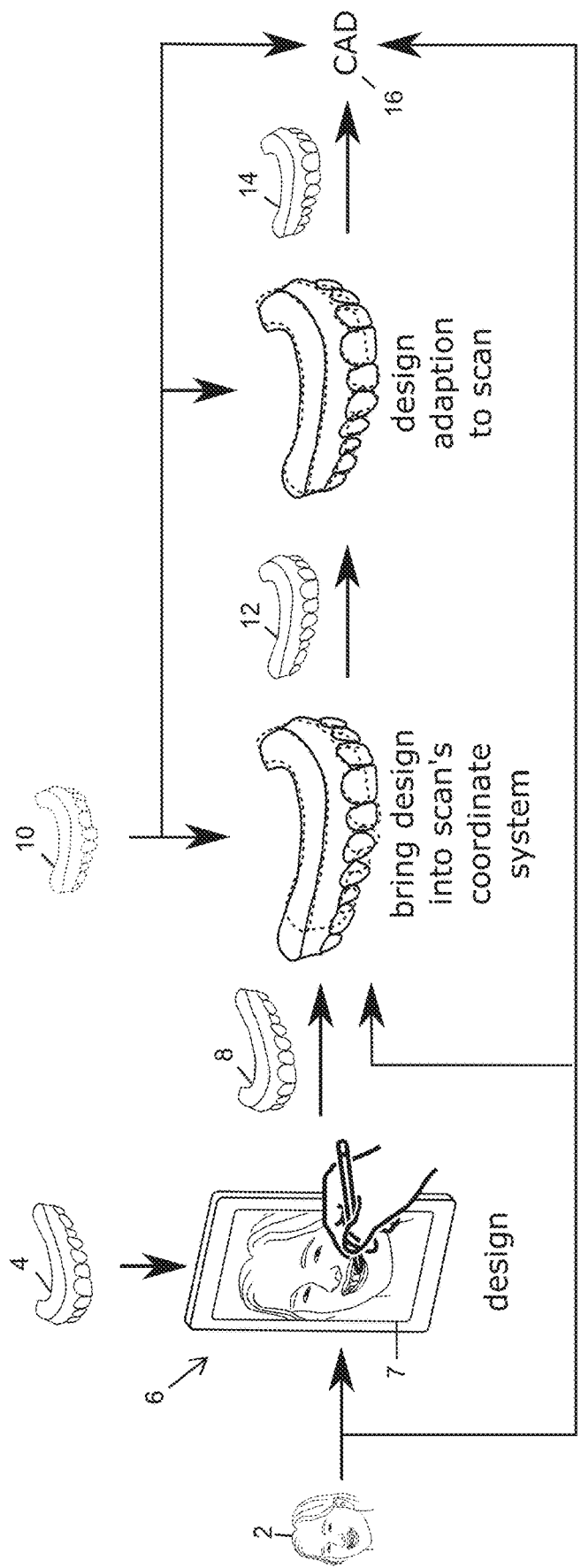
FIG. 1 shows in a diagram the steps to be performed for exporting a three-dimensional design model from an augmented reality application to e.g. a computer-aided design application.

FIG. 1 illustrates an exemplary embodiment of a method for exporting a three-dimensional dental illustrations design model based on a three-dimensional dental library model 4 from an augmented reality application 6. The augmented reality application 6 is adapted to visualize on a display 7 an image of the dental library model 4 rendered by a virtual camera with a preliminary pose and scale in a photo 2 of a face of a patient taken by a camera under a viewing axis of the face of the patient. The photo 2 includes a mouth opening showing the present situation of the patient's dentition. The described method comprises as a first step placing within the augmented reality application 6 the rendered image of the dental library model 4 on the photo 2 and providing tools to modify and/or move the dental library model 4 on the display 7. With these tools, a doctor can in the presence of the patient, remotely, or without the patient, modify the design of the dental library model 4 to obtain a desired dental design model 8. The method comprises as next steps providing a three-dimensional scan model 10 of the present situation of the patient's dentition, aligning the scan model 10 and the present situation of the patient's dentition in the photo 2 to obtain a pose of the scan model 10, and calculating, based on the preliminary pose and scale and the pose of the scan model 10, at least one transformation to bring the desired dental design model 8 and the scan model 10 into a common coordinate system, in particular wherein the desired dental design model 8 is brought to a coordinate system of the scan model 10 to obtain a positioned dental design model 12.

In a next step weighted non-rigid deformations are applied to adapt the shape of the positioned dental design model 12 to the scan model 10 by minimizing a measure of shape difference between the positioned dental design model 12 and the scan model 10 to obtain a modified dental design model 14.

The minimization problem described above belongs to registration problems. A large field of registration is image registration in the two-dimensional space. This can be extended to three-dimensions to solve registration problems with three-dimensional models as it is the case herein. The aim of registration problems is to find a reasonable transformation such that a transformed version of one model is similar to another model. In the case herein it is therefore the aim to find a reasonable transformation such that a transformed version of the positioned dental design model 12 is similar to the scan model 10.

To minimize the difference between two models, here the positioned dental design model and the scan model, an appropriate distance measure has to be applied. Distance measures can be classified as feature- or intensity-based. Feature-based distance measures comprise landmark-based approaches. Feature-based distance measures establish a correspondence between a number of especially distinct points (the so called landmarks) in the two models. Knowing the correspondence between a number of points in the models, a transformation is then determined to map one model to another model, here the positioned dental design model 12 to the scan model 10. Intensity-based approaches compare intensity patterns in the models. An intensity-based distance measure is e.g. the sum of squared differences (SSD). This distance measure measures the energy contained in the difference model of e.g.

the positioned dental design model 12 and the scan model 10. Other distance measures are cross-correlation or using mutual information. There are also methods that combine intensity-based and feature-based distance measures which could also be applied in the present minimization problem.

In addition, a family of functions and the calculation of the parameters of the mapping function must be selected. The simplest case is to use only translation. More parameters have to be calculated by using affine or non-rigid transformations. Non-rigid deformations shall be used to transform the positioned dental design model 12 to the scan model 10.

The transformations can be classified as global or local transformations. By using global transformations one set of parameters is calculated for the whole model. Thus, a global transformation consists of one function which is applied to the whole model. By using local transformations the model is divided into several areas. Parameters are calculated for each area individually. Therefore, each area can be deformed differently. A local transformation therefore consists of several functions, each applied to an area.

The transformations or deformations can be performed by various methods. One approach is to use surface deformation methods as e.g. the as-rigid-as-possible deformation of a polygon mesh. There are a number of variations of these deformation methods. The overall idea is to preserve certain properties of a given set of control points. Another method is the iterative closest points (ICP) algorithm which achieves a deformation in order to match the geometry of the positioned dental design model locally. The problem is to estimate a transformation, which will map the polygon mesh of one model, e.g. the positioned dental design model 12 onto a polygon mesh of another model, e.g. the scan model 10. The first step of the ICP algorithm is to find for the vertices of the polygon model of the positioned dental design model 12 the closest vertices of the polygon mesh of the scan model 10. The second step is to find the transformation that minimizes the distance between the vertices of the transformed polygon mesh of the positioned dental design model 12 and the vertices of the polygon mesh of the scan model 10. In a third step the estimated transformation is applied to the polygon mesh of the positioned dental design model. If the previously determined desired convergence has not been achieved, the algorithm is executed again from the first step.

An option for improving speed and smoothness of the deformation is to use a reduced mesh or proxy mesh, perform the deformation on the reduced mesh or proxy mesh, and perform in a last step an interpolation for the original resolution mesh.

Figure 2:
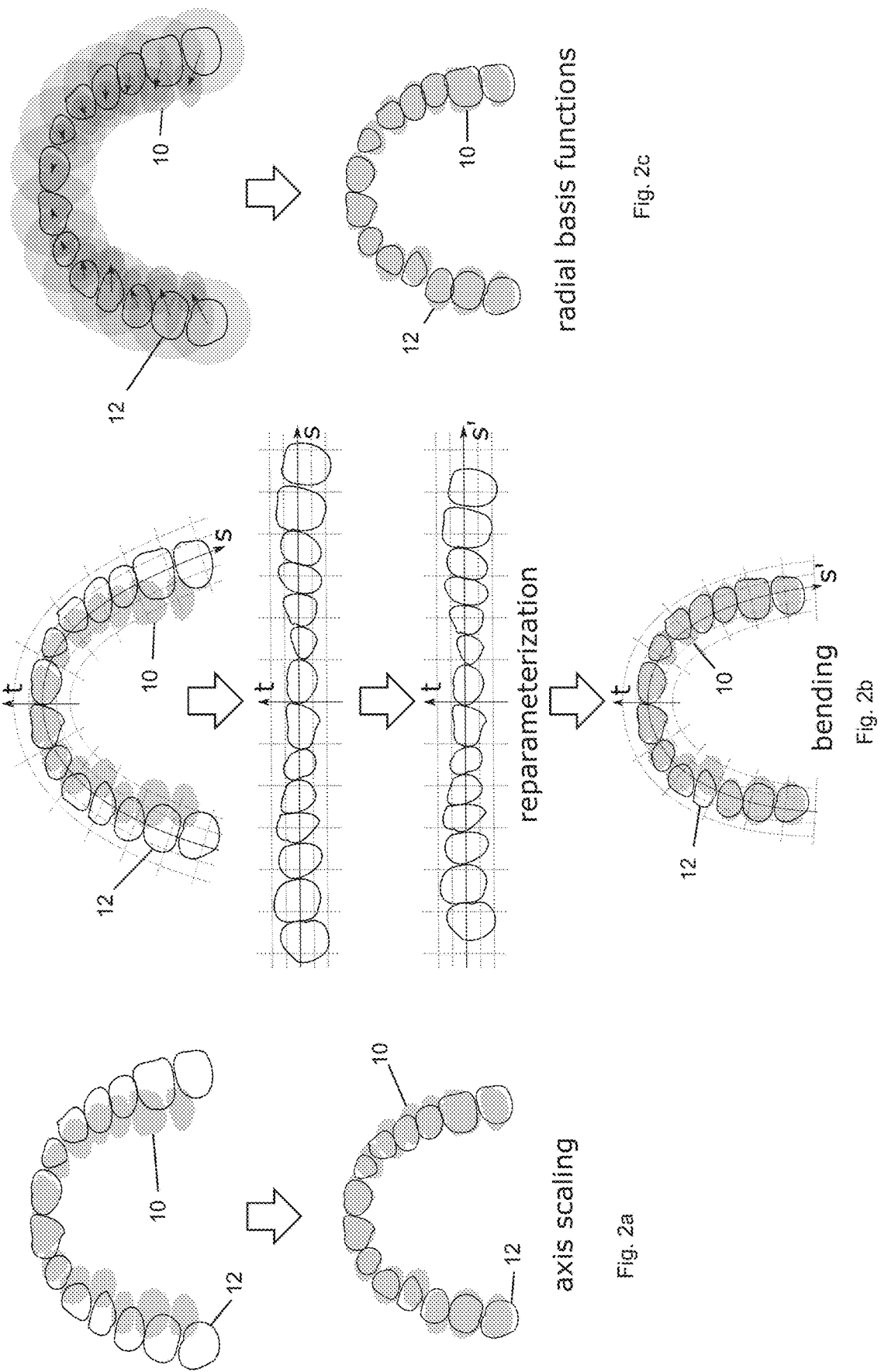
FIG. 2a shows an illustration of a possible space deformation method that can be applied as a non-rigid deformation.
FIG. 2b shows an illustration of a possible space deformation method that can be applied as a non-rigid deformation.
FIG. 2c shows an illustration of a possible space deformation method that can be applied as a non-rigid deformation.

Another approach to perform non-rigid deformations is to use space deformation methods. Possible space deformation methods that can be applied as non-rigid deformations are illustrated in FIGS. 2a-c. FIG. 2a shows scaling along the coordinate axes with potentially different scaling factors for the x, y and z axes. This method can be used to achieve a rough alignment of the scan model 10 to the positioned dental design model 12.

Other methods are freeform deformation or cage deformation that requires specifying a hull which is deformed. This can be achieved by approximating a supporting curve s for each model and computing offset points along the curve. As it is illustrated in FIG. 2b, support curves can also be used to define coordinate systems. In the example of a jaw such a curve roughly follows the jaw arch in a smooth way. If support curves are computed for the scan model 10 and the positioned dental design model 12, the vertices of the scan model 10 can be deformed by transforming them first into the curved coordinate system s,t for the scan model 10. As a next step, a reparameterization or mapping along the curve can be applied to achieve a stretching along the curve and to obtain a mapping s',t. In a following step, an inverse transformation from the curved coordinate system of the positioned dental design model 12 back to a cartesian coordinate system is applied. This results in a transformed positioned dental design model 12 which is deformed to better match the shape of the scan model 10.

Another method is illustrated in FIG. 2c. Radial basis functions can be used to deform the positioned dental design model 12. A radial basis function is a real-valued function whose value only depends on the distance to a fixed point, e.g. the origin or a control point. Usually Euclidian distance is used but also other metrics are thinkable. An often used form for registration with radial basis functions is using thin-plate splines. Thin-plate splines have an elegant algebra expressing the dependence of the physical bending energy of a thin metal plate on point constraints. A set of vectors to describe the deformation, e.g. from the positioned dental design model 12 to the scan model 10 is given. For every vertex of the positioned dental design model 12, the resulting deformation is computed by a weighted average of the vectors depending on the respective distance of the vertex to the starting point of the vectors, i.e. the control point.

Figure 3:
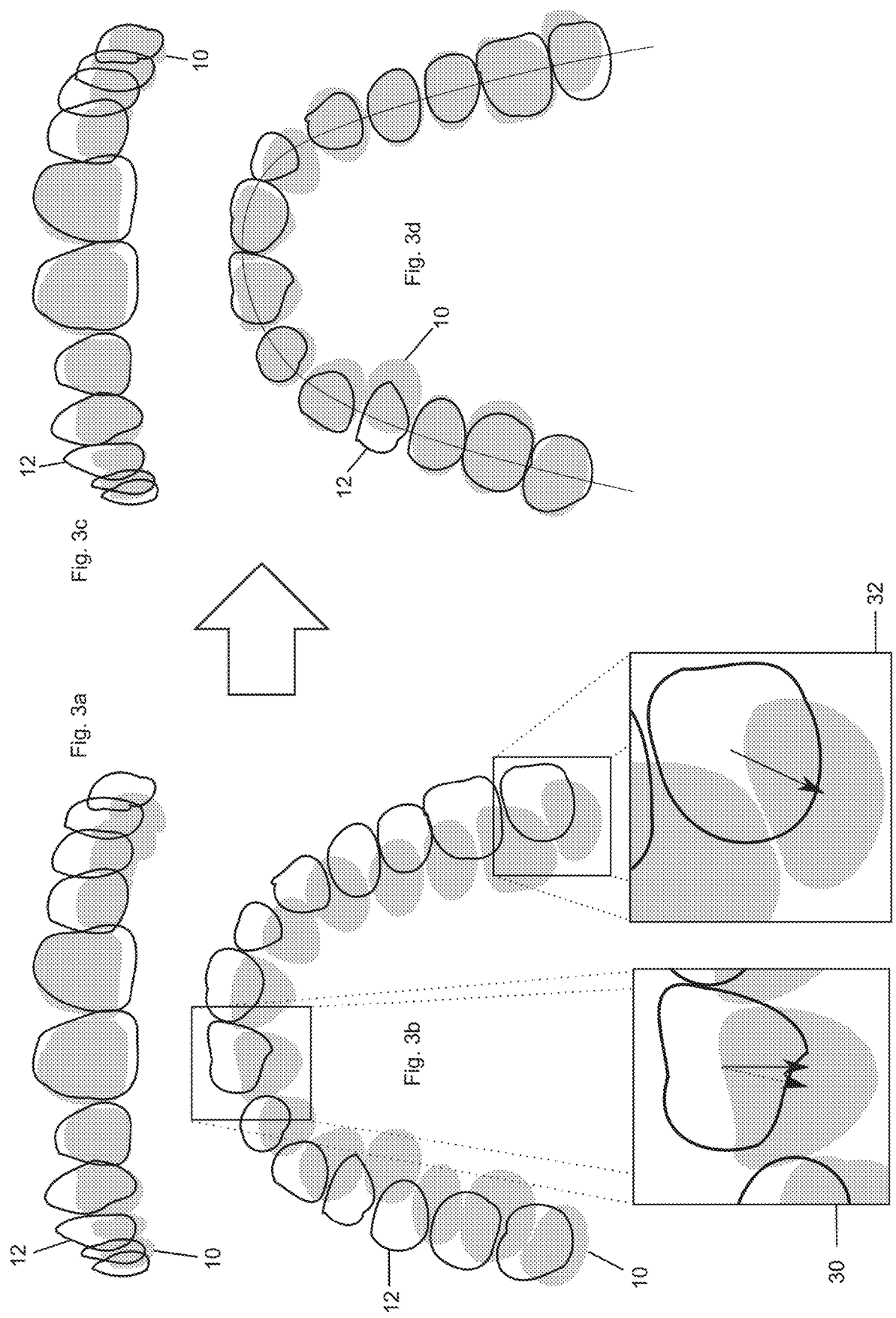
FIG. 3a shows how movements caused by non-rigid deformations are controlled by weights.
FIG. 3b shows how movements caused by non-rigid deformations are controlled by weights.
FIG. 3c shows how movements caused by non-rigid deformations are controlled by weights.
FIG. 3d shows how movements caused by non-rigid deformations are controlled by weights.

Movements of the vertices of the positioned dental design model 12 caused by non-rigid deformations can be controlled by weights as it is illustrated in FIGS. 3a-d. FIGS. 3a and 3b show a scan model 10 and a positioned dental design model 12 of a jaw in an unaligned state. FIG. 3a illustrates the two models from the front, and FIG. 3b illustrates the two models from above. As it can be seen in FIG. 3a the scan model 10 and the positioned dental design model 12 already look aligned for the incisors perpendicular to the viewing axis because the positioned dental design model was designed in this position while movements perpendicular to the viewing axis for the molars of the scan model 10 are still needed to match the molars of the positioned dental design model 12. In FIG. 3b it can be seen that movements along the viewing axis are still needed for the incisors, the molars and the teeth in between of the scan model 10 to match the teeth of the positioned dental design model 12. In the cut-outs 30 and 32 of FIG. 3b the arrows show which movements are allowed for the vertices of the corresponding tooth. The arrows show the directions in which the relevant area of the scan model 12 is allowed to move. Cut-out 30 shows an incisor to its vertices only movements along the viewing axis are allowed to apply. Only movements in the direction of the solid arrow are allowed. Movements in other directions, e.g. movements in the direction of the dashed arrow are restricted. In cut-out 32 a molar is illustrated to its vertices movements along the viewing axis and movements in other directions are allowed to apply. FIGS. 3c and 3d show the scan model 10 and the positioned dental design model 12 of the jaw in an aligned state after the appropriately permitted movements for each vertex have been applied. FIG. 3c illustrates the two aligned models from the front, and FIG. 3d illustrates the two aligned models from above.

Applying weighted non-rigid deformations allows to have significant control over movements of the positioned dental design model 12. The positioned dental design model 12 is deformed to better match the shape of the scan model 10 while at the same time the desired dental design model 8 that the user designed in the augmented reality application 6 mainly in the front region of the dentition including the incisors can be preserved.

The model that is obtained after the deformations have been applied to the positioned dental design model 12 is the dental design model that can be exported to e.g. a computer-aided design application 16.

Figure 4:
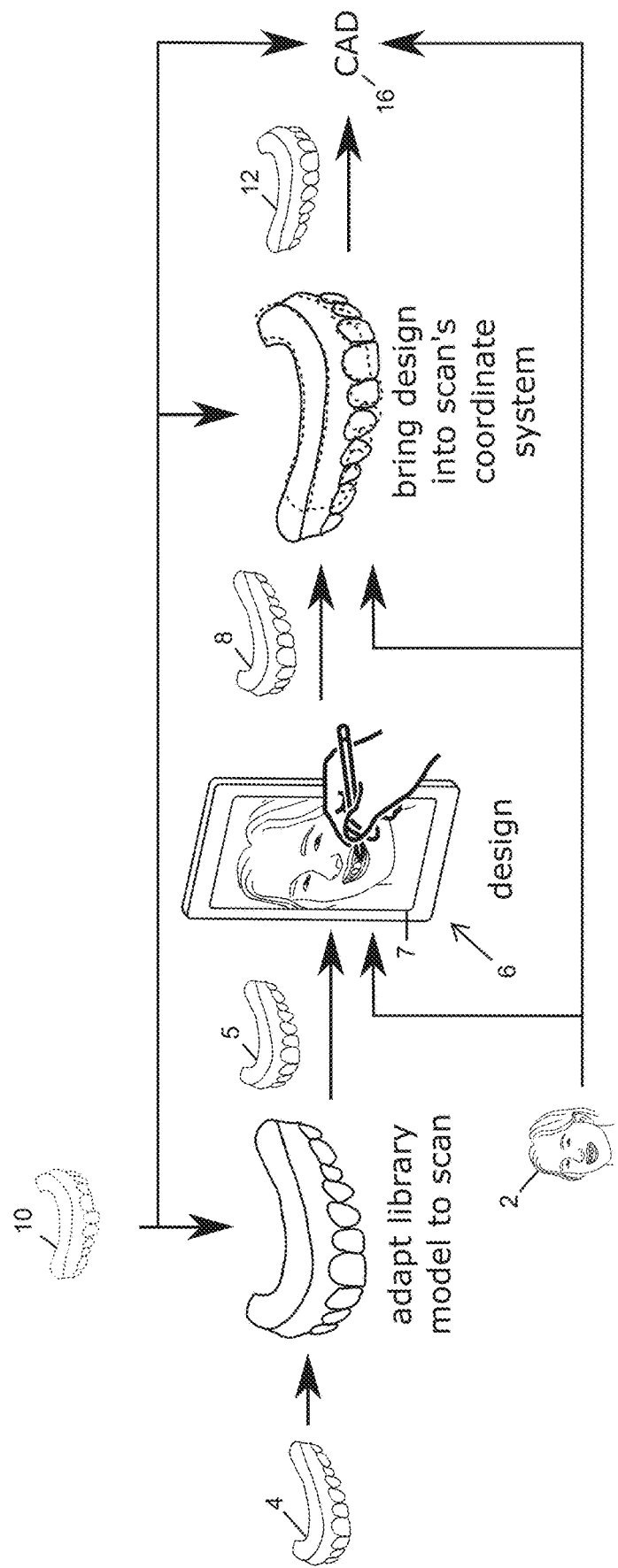
FIG. 4 shows in a diagram the steps to be performed for exporting a three-dimensional design model from an augmented reality application to a computer-aided design application if a three-dimensional scan model of the present situation of the patient's dentition is available before using the augmented reality application.

FIG. 4 illustrates another method for exporting a three-dimensional dental design model from an augmented reality application 6 to e.g. a computer-aided design application 16 if a three-dimensional scan model 10 of the present situation of the patient's dentition is available before using the augmented reality application 6. Therefore, the first step of the method comprises adapting a three-dimensional dental library model 4 to the scan model 10 with weighted non-rigid deformations by minimizing a measure of shape difference between the scan model 10 and the three-dimensional dental library model 4. The restrictions for movements caused by the non-rigid deformations controlled by the applied weights are the same as described above. The result of this first step is a modified dental library model 5. The method comprises as a next step placing within the augmented reality application 6 the modified dental library model 5 on a photo 2 of a face of a patient including a mouth opening showing at least part of the present situation of the patient's dentition and providing tools to modify and/or move the modified dental library model 5 on the display 7. With these tools, a doctor can in presence of the patient, remotely or without the patient, modify the design of the modified dental library model 5 to obtain a desired dental design model 8. Because the modified dental library model 5 is already adapted to the scan model 10 of the patient by weighted non-rigid deformations, the visualization of this model on the photo 2 in the augmented reality application 6 is more realistic. Consequently, designing a desired dental design model 8 based on the modified dental library model 5 requires less time compared to designing a desired dental design model 8 based on a dental library model 4 as disclosed in claim 1 and illustrated in FIG. 1. The reason for this is that fewer adjustments are needed because the modified dental library model 8 is already adapted to the scan model 10 and therefore already matches reasonably the dentition of the patient and thus the present situation of the patent's dentition in the photo 2. The method comprises as next steps aligning the scan model 10 and the present situation of the patient's dentition in the photo 2 to obtain a pose of the scan model 10, and calculating, based on the preliminary pose and scale and the pose of the scan model 10, at least one transformation to bring the desired dental design model 8 and the scan model 10 into a common coordinate system, in particular wherein the desired dental design model 8 is brought to a coordinate system of the scan model 10 to obtain a positioned dental design model 12. This model is the dental design model that can be exported to e.g. a computer-aided design application 16.

In some embodiments, the present disclosure is implemented using a system having a camera, a processor, an electronic data storage unit, and a display. The camera can be a standard camera, an infrared dot-projection detector, flood illuminator camera, structured-light three-dimensional scanner, standard infrared detector, ultrasonic imaging device, Doppler detector, or any other suitable visualization system capable of capturing information related to a patient's dentition. The processor can be a single processor having one or more cores, or a plurality of processors connected by a bus, network, or other data link. The electronic data storage unit can be any form of non-transitory computer-readable storage medium suitable for storing the data produced by the system. The display can be any display suitable for displaying a digital color or grayscale image.

In some embodiments, the camera, processor, electronic data storage unit, and digital display are components of a single device. The single device may be a smartphone, tablet, laptop computer, personal digital assistant, or other computing device. In some embodiments, the processor is in communication over a network, which could be wired or wireless, with an external processor used for performing one or more calculation steps and/or a network-attached electronic data storage unit. In some embodiments, the present disclosure makes use of cloud computing to perform one or more calculations steps remotely and/or remote storage to enable the storage of data remotely for collaborative or remote analysis. In some embodiments, the system comprises a plurality of graphical user interfaces to permit multiple users to view or analyze the same data.

In some embodiments, the system operates to provide one or more users with a visualization of a virtual dental model of a patient's teeth, which may be altered to visualize the effect of one or more dental or orthodontic alterations. In some embodiments, this allows the one or more users to visualize a "before" dentition image, i.e., the appearance of a patient's dentition prior to a dental or orthodontic procedure, and an "after" dentition image, i.e., a representation of the expected appearance of a patient's dentition after a proposed dental or orthodontic procedure.

In some embodiments, the system operates by capturing information related to a patient's dentition using a camera, creating a model of the patient's dentition on a processor, fitting a model of a proposed post-alteration dentition to the patient's dentition on the processor, coloring the model of the proposed post-alteration dentition to match an expected real post-alteration coloration, and displaying the fitted model of the proposed post-alteration dentition in place of the patient's actual dentition on a display which otherwise shows the patient's actual facial features. The information related to a patient's dentition, the model of the patient's dentition, and the model of the proposed post-alteration dentition may be stored on an electronic data storage unit. In some embodiments, the operations are performed in real-time.

In some embodiments, a user interface is configured such that a user may view the "before" dentition image and the "after" dentition image simultaneously either side-by-side or with a full or partial overlay.

Where used herein, the term "non-transitory" is a limitation on the computer-readable storage medium itself—that is, it is tangible and not a signal—as opposed to a limitation on the persistence of data storage. A non-transitory computer-readable storage medium does not necessarily store information permanently. Random access memory (which may be volatile, non-volatile, dynamic, static, etc.), read-only memory, flash memory, memory caches, or any other tangible, computer-readable storage medium, whether synchronous or asynchronous, embodies it.

Although the invention is illustrated above, partly with reference to some preferred embodiments, it must be understood that numerous modifications and combinations of different features of the embodiments can be made. All of these modifications lie within the scope of the appended claims.

The invention claimed is:

1. A method for exporting a three-dimensional dental design model based on a three-dimensional dental library model (4) from an augmented reality application (6), the augmented reality application (6) being adapted to visualize on a display (7) an image of the dental library model (4) rendered by a virtual camera with a preliminary pose and scale in a photo (2) of a face of a patient taken by a camera under a viewing axis to the face of the patient, the photo (2) including a mouth opening showing at least part of the present situation of the patient's dentition, the method comprising:

placing within the augmented reality application (6) the rendered image of the dental library model (4) on the photo (2) and providing tools to modify and/or move the dental library model (4) on the display (7) to obtain a desired dental design model (8), providing a three-dimensional scan model (10) of the present situation of the patient's dentition, aligning the scan model (10) and the present situation of the patient's dentition in the photo (2) to obtain a pose of the scan model (10), calculating, based on the preliminary pose and scale and the pose of the scan model (10), at least one transformation to bring the desired dental design model (8) and the scan model (10) into a common coordinate system to obtain a positioned dental model (12), adapting the positioned dental design model (12) to the scan model (10) with non-rigid deformations by minimizing a measure of shape difference between the positioned dental design model (12) and the scan model (10) to obtain a modified dental design model (14) as the dental design model for export, and determining for the desired dental design model (12) visible and non-visible regions thereof by taking into account the position in respect to the mouth opening and the viewing axis, wherein weighted non-rigid deformations are used to adapt the desired dental design model (12) to the scan model (10), wherein movements caused by the non-rigid deformations and which are perpendicular to the viewing axis are restricted more for the visible regions than such movements for the non-visible regions which is achieved by applying low weights to movements perpendicular to the viewing axis of the visible regions and higher weights to movements perpendicular to the viewing axis of the non-visible regions.

2. The method according to claim 1, comprising wherein the visible regions comprise front regions including incisors and the non-visible regions comprise rear regions including molars, wherein weighted non-rigid deformations are used to adapt the positioned dental design model (12) to the scan model (10), movements caused by the non-rigid deformations and which are perpendicular to the viewing axis are restricted more for the front regions including incisors than such movements for the rear regions including molars which is achieved by applying low weights to movements perpendicular to the viewing axis of the front regions and higher weights to movements perpendicular to the viewing axis of the rear regions.

3. The method according to claim 2, comprising wherein the weights used in the weighted non-rigid deformations and applied to movements perpendicular to the viewing axis of the positioned dental design model (12), gradually increase from the front regions including incisors to the rear regions including molars.

4. The method according to claim 1, comprising wherein the weights used in the weighted non-rigid deformations and applied to movements perpendicular to the viewing axis of the positioned dental design model (12), gradually increase from the visible regions to the non-visible regions.

5. The method according to claim 1, comprising applying weighted non-rigid deformations, wherein by applying weighted non-rigid deformations, movements along the viewing axis are allowed for the positioned dental design model (12) by allowing to apply the same high weights to the movements along the viewing axis of the positioned dental design model (12).

6. The method according to claim 1, comprising, wherein the non-rigid deformations comprise shearing, skewing, uniform and/or non-uniform scaling.

7. The method according to claim 1, comprising, exporting the modified dental design model (14) to an other application, wherein exporting comprises one or more of the following:

generating an export file comprising the modified dental design model (14), the modified dental design model (14) is exported in a file together with the scan model (10), the other application is an external application, the other application is a computer-aided design application (16), and/or the export file is in STL file format.

8. A computer programme product comprising programme code which is stored on a non-transitory machine-readable medium, the non-transitory machine-readable medium comprising computer-executable instructions for performing the method according to claim 1.

9. A method for exporting a three-dimensional dental design model based on a three-dimensional dental library model (4) from an augmented reality application (6), the method comprising:

retrieving a three-dimensional scan model (10) of the present situation of a patient's dentition, adapting the three-dimensional dental library model (4) to the scan model (10) with non-rigid deformations by minimizing a measure of shape difference between the dental library model (4) and the scan model (10) to obtain a modified dental library model (5), placing within the augmented reality application (6) an image of the modified dental library model (5), rendered by a virtual camera with a preliminary pose and scale in a photo (2) of the face of the patient taken by a camera under a viewing axis to the face of the patient, the photo (2) including a mouth opening showing at least part of the present situation of the patient's dentition, on the photo (2) and providing tools to modify and/or move the modified dental library model (5) on a display (7) to obtain a desired dental design model (8), aligning the scan model (10) and the present situation of the patient's dentition in the photo (2) to obtain a pose of the scan model (10), calculating, based on the preliminary pose and scale and the pose of the scan model (10), at least one transformation to bring the desired dental design model (8) and the scan model (10) into a common coordinate system, wherein the desired dental design model (8) is brought to a coordinate system of the scan model (10) to obtain a positioned dental design model (12)

wherein the non-rigid deformations are weighted and are used to adapt the three-dimensional dental library model (4) to the scan model (10).

10. The method according to claim 9, comprising wherein the non-rigid deformations comprise shearing, skewing, uniform and/or non-uniform scaling.

11. The method according to claim 9, comprising exporting the positioned dental design model (12) to an other application, wherein exporting comprises one or more of the following:

generating an export file comprising the positioned dental design model (12), the positioned dental design model (12) is exported in a file together with the scan model (10), the other application is an external application, the other application is a computer-aided design application (16), and/or the export file is in STL file format.

12. A computer programme product comprising programme code which is stored on a non-transitory machine-readable medium, the non-transitory machine-readable medium comprising computer-executable instructions for performing the method according to claim 9.

13. A method for exporting a three-dimensional dental design model based on a three-dimensional dental library model (4) from an augmented reality application (6), the augmented reality application (6) being adapted to visualize on a display (7) an image of the dental library model (4) rendered by a virtual camera with a preliminary pose and scale in a photo (2) of a face of a patient taken by a camera under a viewing axis to the face of the patient, the photo (2) including a mouth opening showing at least part of the present situation of the patient's dentition, the method comprising:

placing within the augmented reality application (6) the rendered image of the dental library model (4) on the photo (2) and providing tools to modify and/or move the dental library model (4) on the display (7) to obtain a desired dental design model (8), providing a three-dimensional scan model (10) of the present situation of the patient's dentition, aligning the scan model (10) and the present situation of the patient's dentition in the photo (2) to obtain a pose of the scan model (10), calculating, based on the preliminary pose and scale and the pose of the scan model (10), at least one transformation to bring the desired dental design model (8) and the scan model (10) into a common coordinate system to obtain a positioned dental model (12), adapting the positioned dental design model (12) to the scan model (10) with non-rigid deformations by minimizing a measure of shape difference between the positioned dental design model (12) and the scan model (10) to obtain a modified dental design model (14) as the dental design model for export, and applying weighted non-rigid deformations, wherein by applying weighted non-rigid deformations, movements along the viewing axis are allowed for the positioned dental design model (12) by allowing to apply the same high weights to the movements along the viewing axis of the positioned dental design model (12).

* * * * *